US006409383B1

(12) United States Patent
Wang et al.

(10) Patent No.: US 6,409,383 B1
(45) Date of Patent: Jun. 25, 2002

(54) AUTOMATED AND QUANTITATIVE METHOD FOR QUALITY ASSURANCE OF DIGITAL RADIOGRAPHY IMAGING SYSTEMS

(75) Inventors: Xiaohui Wang, Pittsford, NY (US); Richard L. Vanmetter, Washington, DC (US); David L. Foos; David J. Steklenski, both of Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/525,089

(22) Filed: Mar. 14, 2000

(51) Int. Cl.$^7$ ................................................. G01D 18/00
(52) U.S. Cl. ...................................... 378/207; 378/204
(58) Field of Search .................................. 378/207, 204

(56) References Cited

U.S. PATENT DOCUMENTS

| 5,420,441 A | | 5/1995 | Newman et al. | |
| 5,544,238 A | * | 8/1996 | Galkin | 378/207 |
| 5,591,968 A | | 1/1997 | Grillet | |
| 6,231,231 B1 | * | 5/2001 | Farrokhnia et al. | 378/207 |

FOREIGN PATENT DOCUMENTS

WO     WO 95/31869     11/1995

OTHER PUBLICATIONS

J. Anthony Seibert, "Photostimulable Phosphor System Acceptance Testing", AAPM Medical Physics, Monograph No. 20: Specification, Acceptance Testing and Quality Control of Diagnostic X-ray Imaging Equipment, 1991.
Hiroshi Fujita, Du–Yih Tsai, Takumi Itoh, Kunio Doi, Junji Morishita, Katsuhiko Ueda, Akiyoshi Ohtsuka, "A Simple Method for Determining the Modulation Transfer Function in Digital Radiography", IEEE Transactions on Medical Imaging, vol. 1, No. 1, 1992.
Stephen E. Reichenbach, Stephen K. Park, Ramkumar Narayanswamy, "Characterizing Digital Image Acquisition Devices", Optical Engineering, vol. 30, No. 2, 1991.
Walter Huda, Manuel Arreola, Xhenxue Jing, "Computed Radiography Acceptance Testing", SPIE Symposium on Medical Imaging, vol. 2432, 1995.
Hamid Jafroudi, Dot Steller, Matthew Freeman, Seong Ki Mun, "Quality Control on Storage Phosphor Digital Radiography Systems", SPIE Symposium on Medical Imaging, vol. 2432, 1995.
Terese M. Bogcki, "Acceptance Testing and Quality Control of Computed Radiography Systems", technical and Scientific, Bulletin No. 8792038, Eastman Kodak Company.
Kenneth A. Fetterly, Ramesh Avula, Nicholas J. Hangiandreou, "Development and Implementation of An Automated, Quantitative Film Digitizer Control Program", SPIE Symposium on Medical Imaging, 1999.
Ehsan Samei, Michael J. Flynn, "A Method for Measuring The Presampled MTF of Digital Radiographic Systems Using An Edge Test Device", Medical Physics 25 (1), Jan. 1998.
Ali J. Tabatabai, O. Robert Mitchell, "Edge Location to Subpixel Values in Digital Imagery", IEEE Transaction on Pattern Analysis and Machine Intelligence, vol. 6, 1984.
William H. Press, Saul A. Teukolsky, William T. Vetterling, Brian P. Flannery, "Numerical Recipes in C: The Art of Scientific Computing", 2nd. Edition, Cambridge University Press, 1996.

* cited by examiner

*Primary Examiner*—Drew Dunn
*Assistant Examiner*—Therese Barber
(74) *Attorney, Agent, or Firm*—William F. Noval

(57) ABSTRACT

A phantom for use in measuring parameters in a digital radiography image system comprising a substantially rectangular member of an x-ray attenuating material; a first rectangular array of landmarks associated with the member for use in geometry measurements; a set of regions associated with the central position of the member for exposure linearity and accuracy measurement and a set of sharp angular edges part of one of the regions for modulation transfer function measurements.

15 Claims, 6 Drawing Sheets

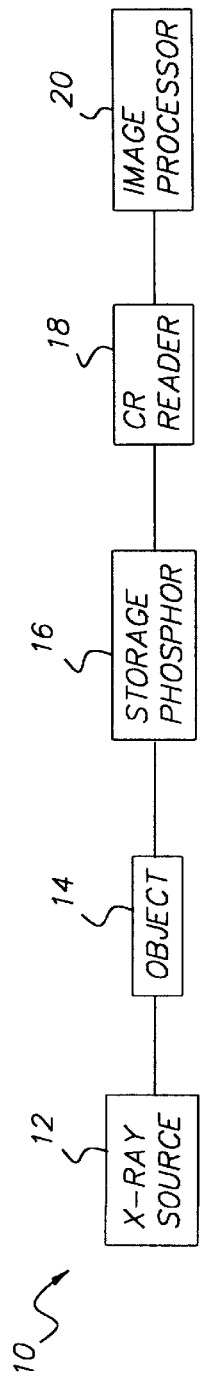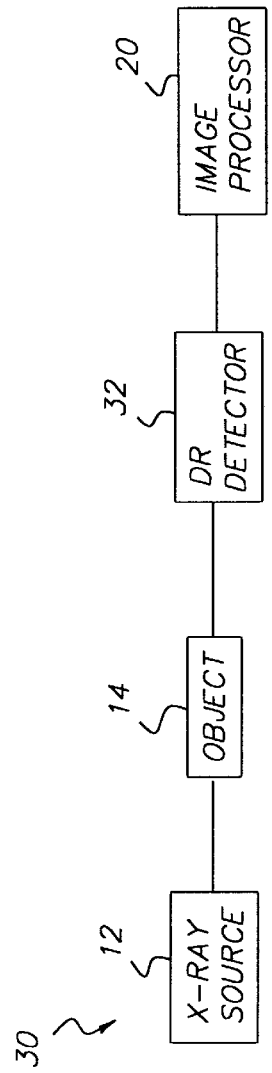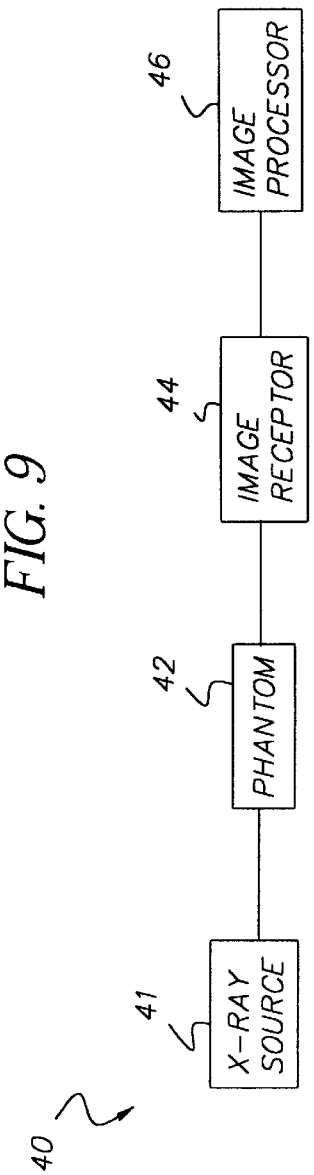

AUTOMATED AND QUANTITATIVE METHOD FOR QUALITY ASSURANCE OF DIGITAL RADIOGRAPHY IMAGING SYSTEMS

FIELD OF THE INVENTION

This invention relates in general to an automated method for the quality assurance (QA) of x-ray digital radiography imaging systems. More particularly, it relates to such a method that can provide a simple and quick way to quantitatively measure the characteristics of storage phosphor-based computed radiography (CR) imaging systems and direct-digital flat-panel detector-based direct radiography (DR) imaging systems.

BACKGROUND OF THE INVENTION

There are a number of important parameters that together characterize the performance of x-ray imaging systems. For CR and DR, most of these parameters are common to both, yet some are unique to the particular type of system. Those common parameters include spatial resolution, noise, detective efficiency, exposure response, dark image signal level, and artifacts etc.

For CR and DR, the modulation transfer function (MTF) of the imaging system is often used to characterize the system spatial resolution. MTF is a 2D (two-dimensional) function of spatial frequency and is usually measured for both x and y directions of the acquired image. There have been developed three major types of techniques for MTF measurement: resolution target, angular slit and angular edge. The resolution target technique depends on imaging either a commercially available bar-target or a star-pattern target (J. Anthony Seibert, "Photostimulable Phosphor System Acceptance Testing," AAPM Medical Physics Monograph No. 20: Specification, Acceptance Tesing and Quality Control of Diagnostic X-ray Imaging Equipment, 1991) or a custom-made bar target of varying resolution (J. Daniel Newman, Daniel K. McBridge, James C. Montoro, "Automatic Technique for Calibrating A Storage Phosphor Reader," U.S. Pat. No. 5,420,441, 1995). In this technique, the MTF is estimated either using a human observer to identify the blur frequency point of the target or calculating the visibility modulation. The error of the estimation depends on the orientation/resolution of the target and the subjective criteria of the observer. It requires that he target be perfectly aligned in the x or y direction, and the severity of the error increases when the target resolution is close to the Nyquist frequency of the imaging system.

Another method that makes use of a narrow slit can be used to measure the line spread function, followed by Fourier transformation to obtain the MTF of the imaging system in the slit transverse direction (Hiroshi Fujita, Du-Yih Tsai, Takumi Itoh, Kunio Doi, Junji Morishita, Katsuhiko Ueda, and Akiyoshi Ohtsuka, "A Simple Method for Determining the Modulation Transfer Function in Digital Radiography," IEEE Transactions on Medical Imaging, Vol. 11, No. 1, 1992). In this technique, to obtain the MTF in the x or y direction, the orientation of the slit must be placed at a slight angle with the y or x direction in order to achieve super sampling for aliasing reduction. The width of the slit is required to be much narrower than the sampling pitch (pixel size) of the imaging system, and the slit needs to be long enough to cover at least one pixel in the slit transverse direction. Although this is a very accurate method for MTF measurement, it relies on a delicately made, expensive slit target.

A third method makes use of a sharp and straight edge target to measure the edge spread function of the imaging system. The MTF in the edge transverse direction can be obtained from the edge spread function by taking the Fourier transform of it's derivative (Stephen E. Reichenbach, Stephen K. Park, and Ramkumar Narayanswamy, "Characterizing Digital Image Acquisition Devices," Optical Engineering, Vol. 30, No. 2, 1991). Because sharp and straight edges are relatively easy to manufacture accurately, this method is preferred for MTF measurement for the quality assurance of digital radiography imaging systems.

The noise of the imaging system determines the system low-contrast resolution as well as the x-ray detective efficiency etc. The noise characteristics can be described by the noise power spectrum (NPS) of the imaging system, which is also a 2D function of spatial frequency. To obtain the NPS, a flat image region is usually taken for Fourier analysis. Because the system noise level is also x-ray exposure dependent, the NPS is often measured at a certain exposure level to facilitate comparisons among imaging systems.

Detective efficiency is a secondary parameter of the imaging system that can be readily calculated from the system MTF and NPS:

$$DQE(u, v) = DQE(0, 0) \frac{MTF^2(u, v)}{NPS(u, v)}.$$

Exposure response describes the relationship between the output of the imaging system (image pixel values) and the incident x-ray exposure. Ideally, the exposure response or logarithmic exposure response should be linear and equal for all the pixels across the whole image. Response accuracy, linearity, and uniformity are three of the major parameters for exposure response characterization. Exposure accuracy and linearity describes how accurately and linearly the output of the imaging system can track the incident x-ray exposure. Response uniformity describes the inter-pixel response variation. All three parameters are usually measured using the same x-ray spectrum but different exposure levels.

The dark image signal level determines the baseline noise of the imaging system and it is independent of x-ray exposure. For a CR image, this corresponds to the signal level that would result from reading an erased phosphor screen, and for a DR image, this corresponds to the accumulated noise level before the x-ray exposure and during the readout process.

Artifacts may also be present in images. The nature of artifacts is that they are often unpredictable and may take the form of spots, lines and low-frequency modulations etc and can also be periodic or non-periodic. The white and dark spots are usually caused by foreign dust/dirt residing on the image receptor or caused by the bad pixels (DR). There are two major types of line artifacts, periodic (banding), and non-periodic (streaks). Either artifact will result in objectionable image quality if the magnitude is large enough.

There are several other important parameters for image QA that are unique to either CR or DR. For a CR imaging system, a laser beam is used for raster scanning and reading the signal from the storage phosphor screen. Because there are moving optical devices, the image pixel size and the pixel aspect ratio can be spatially variant. The other two important parameters for CR image quality assurance are scan linearity and scan accuracy which are measures of the geometric integrity of the image. Although there is no variable geometry related quality assurance issues for DR because all the imaging pixels are solid state elements manufactured on an evenly distributed grid, the locations of failed pixels and the individual pixel response correction are unique to DR and need to be characterized.

The large number of diversified parameters to be measured for the QA of digital x-ray imaging systems, presents a considerable challenge for designing a quick, accurate, easy to use, and fully automatic method/procedure to conduct the measurements. There have been considerable efforts so far in this area. However, most of the proposed methods rely either on visually reading image pixel values from a computer screen or on printing a test image on film and then using visual examination combined with film densitometer measurements. For example, the methods using film prints and densitometer measurements include (1) the work by J. Anthony Seibert ("Photostimulable Phosphor System Acceptance Testing," AAPM Medical Physics Monograph No. 20: Specification, Acceptance Testing and Quality Control of Diagnostic X-ray Imaging Equipment, 1991), (2) the work by Walter Huda, Manuel Arreola and Xhenxue Jing ("Computed Radiography Acceptance Testing," SPIE Symposium on Medical Imaging 1995, Vol. 2432), (3) the work by Hamid Jafroudi, Dot Steller, Matthew Freeman and Seong Ki Mun ("Quality Control on Storage Phosphor Digital Radiography Systems," SPIE Symposium on Medical Imaging 1995, Vol. 2432), (4) and the several methods by x-ray test target manufacture companies. The latter include the EZ CR Test Tool from Nuclear Associate (100 Voice Raod, Carie Place, N.Y. 11514-0349) and the X-Ray Test Objects for Computed Radiography from FAXiL (Wellcome Wing, Leeds General Infirmary, Great George St., Leeds LS1 3EX, West Yorks, England). However, all these provided methods are limited by the quality of the film printer and densitometer.

Kodak provides a recommendation for the CR QC procedure (Terese M. Bogcki, "Acceptance Testing And Quality Control of Computed Raiography Systems," Technical and Scientific Bulletin No. 8792038, Eastman Kodak Company, 1997). Although this method uses direct image pixel value reading from the quality control workstation (QCW), it is not automatic and still relies on film prints for many of the measurements. The AAPM Task Group No. 10 summarized the testing methods provided by three major CR manufacturers, Kodak, Fuji and Agfa. Some results using the AAPM recommendations were published ("Acceptance testing of Computed Radiography Imaging Systems—An Update," Scientific Exhibit on the Radiology Society of North America' 1998). However, the proposed method itself is still not automatic and is tedious to conduct.

Only a few automated methods have been proposed so far for the QA of digital x-ray imaging systems. For example, the method proposed by J. Daniel Newman, Daniel K. McBridge and James C. Montoro ("Automated Technique for Calibrating A Storage Phosphor Reader;" U.S. Pat. No. 5,420,441, 1995) is based on imaging a specially made phantom and analysis of the phantom image to derive the system performance parameters. These derived parameters are then compared with those corresponding to pre-stored threshold values of a normal imaging system. Decisions are made regarding the system performance based on the comparisons. Similar approaches are also reported by Roland Reitan ("Automated Image Quality Control," PCT/US95/ 31869) and Agfa ("ADC Auto Software Module"). Another approach disclosed by Luc Grillet ("Photostimulable Imaging Plate And Method of Testing A Digital Device for Scanning Such A Plate," U.S. Pat. No. 5,591,968, 1997) uses a phosphor screen on which a special mask pattern is printed for x-ray exposure. The mask pattern is transparent to x-rays but not to the laser beam used in the readout process. Therefore, the latent x-ray signal from the exposure can be read only at location on the phosphor screen where there is no mask pattern. A phantom image is created by this means and the analysis is conducted thereafter. All aforementioned methods, however, have only limited accuracy for MTF measurement because the measurement is derived using a bar-target.

There was proposed use of the angular edge method instead of the bar-target for MTF measurement (Kenneth A. Fetterly, Ramesh Avula and Nicholas J. Hangiandreou, "Development And Implementation of An Automated, Quantitative Film Digitizer Quality Control Program," SPIE Symposium on Medical Imaging 1999), an (Ehsan Samei and Michael J. Flynn, "A Methodfor Measuring The Presampled MTF of Digital Radiographic Systems Using An Edge Test Device", Medical Physics 25(1), January 1998). However, the first method was designed for the film digitizer application only and will be ineffective for CR system performance evaluation. Because the phantom is made by the film printer, its performance is limited by the printer. The second method, however, does not teach how to conduct the measurement automatically.

SUMMARY OF THE INVENTION

This invention relates in general to an automated method for the quality assurance (QA) and quality control (QC) of x-ray digital radiography imaging systems. More particularly, it relates to such a method that can provide a simple and quick way to quantitatively measure the characteristics of storage phosphor-based computed radiography (CR) imaging systems and direct-digital flat-panel detector-based direct radiography (DR) imaging systems.

According to a feature of the present invention, there is provided a phantom for use in measuring parameters in a digital radiography image system comprising:

a substantially flat member of an x-ray attenuating material;

a first array of landmarks associated with said member for use in geometry measurements;

a set of regions associated with the central portion of said member for exposure linearity and accuracy measurement; and a set of sharp angular edges part of one of said regions for modulation transfer function measurements.

According to another feature of the present invention, there is provided in a digital radiographic imaging system including a variable source of x-rays, an x-ray image receptor, and a digital image processor, a method of measuring pre-selected parameters of said system comprising:

erasing the image photoreceptor and exposing said image receptor to a flat field x-ray image at a predetermined x-ray exposure level from said x-ray source to produce a digital flat field x-ray image;

erasing the image receptor immediately after a relatively high x-ray exposure level from said x-ray source followed by reading said image receptor to produce a digital dark erased x-ray image;

exposing said image receptor to x-rays from said x-ray source projected through a phantom having regions of different x-ray attenuation to produce a digital phantom x-ray image; and processing in said digital image processor said digital x-ray images to determine parameters of said digital radiographic imaging system.

ADVANTAGEOUS EFFECT OF THE INVENTION

The invention has the following advantages.

(1) The defined procedure to acquire images is simple and quick to conduct, which helps to reduce system downtime.

(2) The software for image analysis is fully automated. It is fast in computation and can provide quantitative and reliable measurements of system characteristics. The measurements are precise and sensitive.

(3) Eliminates all subjective assessments and third-party measurement device dependence.

(4) The procedure/method makes it possible that one standard can be used by the manufacture, field service and hospital.

(5) The specially designed cassettes holders allow the same target to be used for many cassette types.

BRIEF DESCRIPTION OF THE DRAWINGS

FIGS. 8–10 are block diagrams useful in explaining the invention.

DETAILED DESCRIPTION OF THE INVENTION

Figure 1:
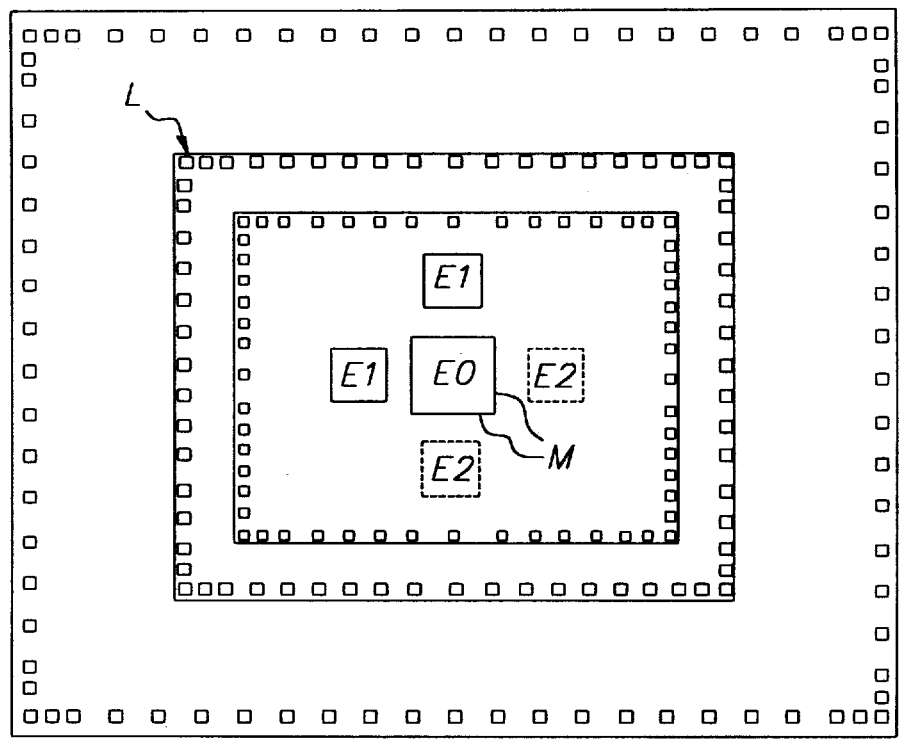
FIG. 1 is a diagrammatic view of a phantom for use in the present invention. The phantom consists of many small square landmarks (L) for geometry measurements, small regions (E0, E1 and E2) for exposure linearity and accuracy measurement, and sharp angular edges (M) for MTF measurements. The phantom is designed to be useful for different image receptor sizes.
Figure 2:
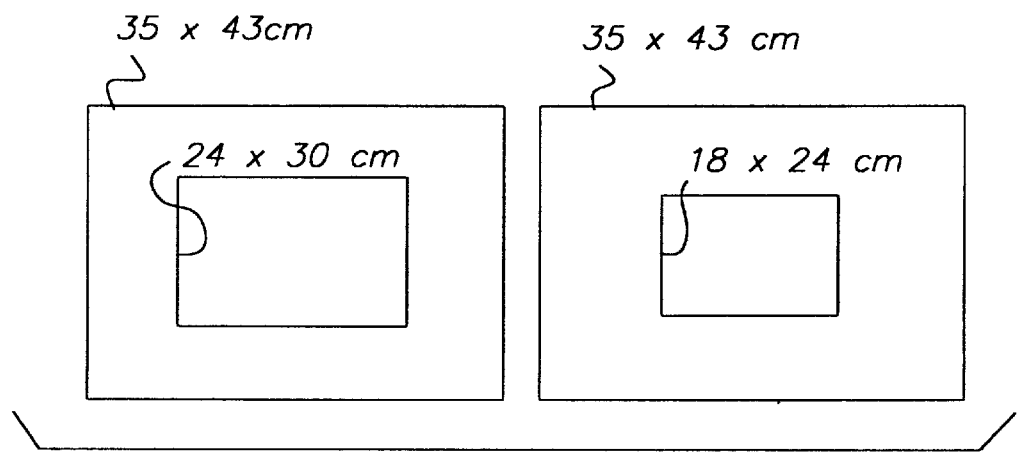
FIG. 2 is a diagrammatic view showing the frames used to center and align the image receptor with the phantom of FIG. 1. The smaller image receptor is placed in the center opening of the frame, then the image receptor and the frame is placed beneath and aligned with the larger phantom along the four sides.
Figure 3B:
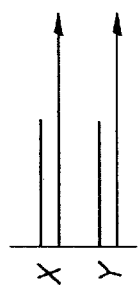
FIGS. 3–7 are diagrammatic views useful in explaining the invention.
Figure 3C:
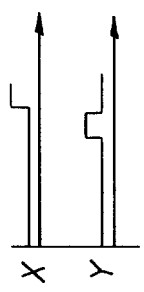
Figure 3D:
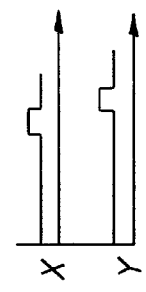
Figure 3A:
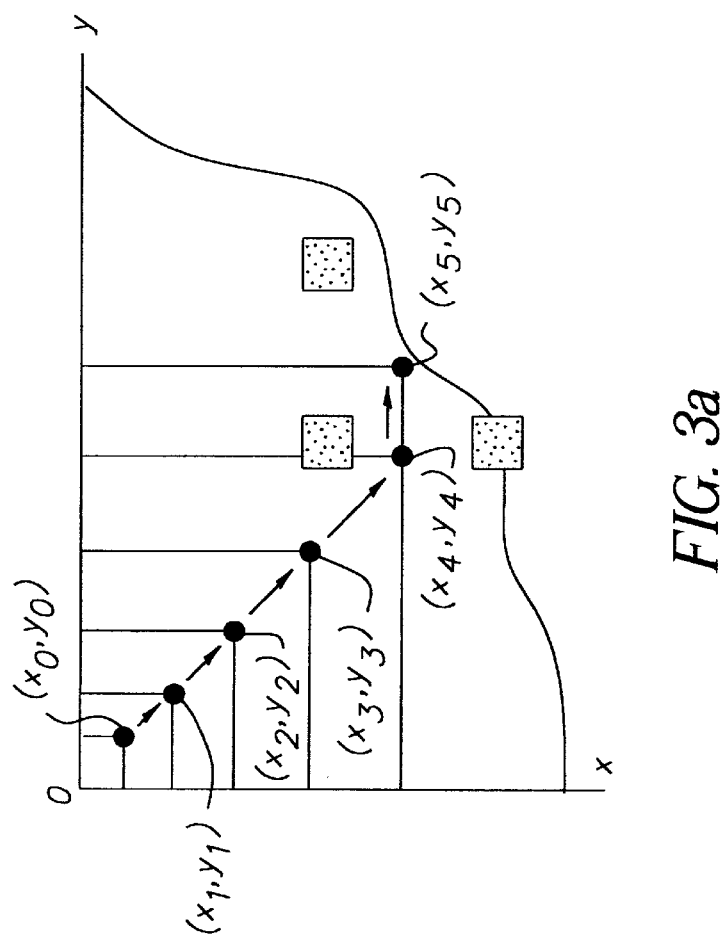

The present invention relates to an automated method for quality assurance of x-ray digital radiography imaging systems including storage phosphor-based computed radiography (CR) imaging systems and direct-digital flat-panel detector-based direct radiography (DR) imaging systems. As shown in FIG. 8, a storage phosphor-based computed radiography imaging system 10 includes an x-ray source 12 which projects x-rays through an object 14 (such as individual's body part) to produce an x-ray image of the object which is recorded as a latent image in storage phosphor 16. The stored x-ray image is read out by CR reader 18 to produce a digital x-ray image. The digital x-ray image is processed by image processor 20, which can be a computer. The processed or original digital x-ray image can be stored, displayed on a video display, transmitted to a remote location, printed out as a hard copy visual image, etc.

The CR reader 18 scans the exposed storage phosphor 16 with a laser beam of one wavelength to emit an optical x-ray image at a second wavelength.

The laser beam is scanned across the storage phosphor in a fast scan direction by a reciprocating galvo mirror or multifaceted polygon mirror, as the storage phosphor is moved past the scanning laser beam in a slow scan direction perpendicular to the fast scan direction. The emitted x-ray light image is detected by a photodetector assembly located in a mirrored collector which converts the x-ray light image into a digital x-ray image.

A direct digital x-ray imaging system 30 is shown in FIG. 9. As shown, x-ray source 12 projects x-rays through object 14 to produce an x-ray image of the object which is detected by DR detector 32. Detector 32 converts the x-ray image directly into a digital image and can include a first detector which converts the x-ray image into a light image and an associated detector which converts the light image into a digital image. Detector 32 can also be of a type which converts the x-ray image directly into a digital image. As with system 10, the digital image is processed by image processor 20.

Referring not to FIG. 10, there is shown an x-ray digital radiography imaging system incorporating the present invention. As shown, system 40 includes an x-ray source 41, phantom 42, image receptor 44 and image processor 46. In a direct digital system, image receptor 44 is that of DR detector 32 shown in FIG. 9. In a CR system, image receptor 44 includes storage phosphor 16 and CR reader 18 shown in FIG. 8. X-ray source 41 includes controls which control the power and duration of x-rays emitted by source 41. Image processor 46 is preferably a computer which includes a digital processor, input devices (keyboard, mouse, trackball), a video display storage (RAM, optical or magnetic disk drive), input/output (I/O), etc. Phantom 42 will be described in greater detail below. According to the present invention, imaging systems parameters are measured as follows.

Due to the complexity of the imaging system parameters to be measured, it is difficult to obtain all the parameters that are required for image quality assurance from single x-ray exposure (image). Therefore, there will be described (1) a physical phantom, (2) a procedure for conducting a minimal number of exposures, and (3) corresponding image analysis methods.

The procedure for conducting the measurements consist of the following steps:

(a) erase the image receptor 44, take a flat field image at a predetermined x-ray exposure level (such as 10 mR) from x-ray source 41, then readout the image for analysis by image processor 46- later on this image is referred to as the flat field image;

(b) erase the image receptor 44 right after a relatively high x-ray exposure level (such as 10 mR) from x-ray source 41, readout the dark image for analysis by image processor—later on this image is referred to as the erased image;

(c) take the image of a testing phantom for analysis—later on this image is referred to as the phantom image.

A set of parameters that describe the system's characteristics are obtained from the three images. These measured parameters are then compared with predefined normal ranges (tolerances) for the QA processes. The phantom image is used for measurement of spatial resolution, exposure response and geometric distortions. Noise and detective efficiency can also be obtained from the test phantom. The erased image is used for dark image noise analysis. The flat field image is used for system noise artifact. and response uniformity inspection.

Phantom Design

The phantom 42 is used to generate reference target objects in an image in order to measure certain system characteristics, such as MTF, exposure response (accuracy and linearity), geometric distortion and noise. For CR systems, geometry related parameters, such as pixel size, aspect ratio, scan tilt, scan linearity and accuracy etc, are obtained by measuring the locations of predefined landmarks in the phantom image. For DR systems, because there is no variable geometric distortion, the landmarks have limited utility. However, these landmarks can still be used as reference points to locate other target objects in the phantom, such as the MTF target and the exposure response target.

The phantom 42 is easy to manufacture with high accuracy and at low cost. The phantom is designed to be durable, compact, light weight, insensitive to temperature related distortion etc., and provides sufficient x-ray attenuation to support the required QA measurements at a reasonable thickness. Because photo-etching metals can satisfy such low cost and high accuracy requirements, and metals generally have stable thermal characteristics, they are good candidates for the phantom material.

There are three major types of metals used in x-ray beam attenuation: copper, aluminum, and lead. Since copper has a higher attenuation coefficient than aluminum at the x-ray beam energy range used for general diagnostic radiography, it is possible to make the phantom thinner. Moreover, the technology for photo-etching copper is well-established. Copper also has inherent advantages over lead for this application because its crystal size is much smaller, which allows much sharper edges to be made. In addition, the use of lead for the phantom material has environmental implications, since it needs to be properly handled and recycled. In the preferred embodiment of this disclosure, the phantom is made of copper.

FIG. 1 shows a diagram of the phantom 42. The copper plate acts as the phantom substrate. Located on the phantom substrate are landmarks (L) that are used as references for the geometry measurements, regions (E0, E1 and E2) for exposure response calculation and the corresponding noise measurement, and sharp angular edges (M) for MTF measurements in the x and y directions. The flat regions in the phantom can be used for artifact examinations, noise, and field uniformity inspection etc. An x-ray dosimeter can also be placed in the flat regions to record the incident x-ray exposure level.

The landmarks (L) can be of any regular or irregular shapes. However, regular shapes, such as circles, rectangles or squares, make the image analysis software straightforward. Squares are the overall preferred shape because they provide sharp and straight pixel-value transitions in both x and y directions. The landmarks can be made from holes directly drilled in the phantom or extra metal attachments, but the approach based on holes is preferred for photoetching or other fabrication processes. Because the geometry related properties of the digital x-ray imaging system usually have the poorest performance near the image boundaries, the landmarks are distributed along the perimeter of the near-maximum rectangle that can be imaged. Furthermore, the distances between the landmarks are also smaller at the corners of the rectangle to enable more accurate geometry characterization.

For the CR application, there are three typical storage phosphor screen sizes, 35×43, 24×30, and 18×24 cm, and the system performance is often different for each screen type. To make the phantom more general and useful, several concentric landmark sets can be made on the phantom plate with each corresponding to a different image receptor size. When the phantom is used with an image receptor of the same size as the phantom, it is placed on top of the image receptor and is simply aligned around all corners. Otherwise, if the phantom is used with a smaller image receptor, a specially made, rigid frame is used to hold, align, and center the image receptor beneath the phantom. The frame has the same size of the phantom and has a hole drilled in its middle to hold the smaller image receptor. Its thickness should be close to that of the image receptor. For any situation, the outer most rectangular set of landmarks in the acquired image are used for geometry characterization.

Region E0 is an angular square hole in the phantom center; it serves as a direct exposure region for exposure response measurement. Its two edges (M) are made very sharp for MTF measurements. Region E2 is the native phantom plate; it represents the x-ray attenuation by the phantom plate. Region E1 uses extra filtration squares (~20 mm) added on top of the phantom plate for additional x-ray attenuation. To achieve enough signal separation between regions E0/E2 and E2/E1, the phantom plate is chosen to be ~1.0–1.5 mm thick copper, and the extra filtration of region E1 is made of small squares of ~2.5–3.0 mm thick copper. A decade of exposure latitude between region E0/E2 and E2/E1 is approximately achieved by this thickness arrangement.

For CR systems, a collector profile is applied to the acquired image signal in order to compensate for the non-uniform detection sensitivity of the system in the fast scan direction. Because this collector profile is only applied in the fast (lasy) scan direction, i.e., for the same line of pixels along the slow (transport) scan direction, the added value that comes from the collector profile compensation is constant. Therefore, in a preferred embodiment of the present disclosure, there are two E1 regions and two E2 regions. This arrangement ensures that no matter in which direction the fast scan is conducted relative to the phantom, there is always a column of region E1, E0, and E2 such that their centers are in the same line of pixels along the image slow scan direction. By selecting one of the E1 regions and one of the E2 regions that both are in the slow scan direction for exposure measurement, the collector profile effect has been kept constant for all regions.

According to the invention, the MTF of the digital x-ray imaging system is measured in both x and y directions using the angular edge technique. Theoretically, any reasonable long and sharp edge transition can be utilized for this purpose. However, because the x-ray beam used in practice is divergent and the edge has a finite thickness, the formation of the edge transition on the image receptor after x-ray penetration may not be sharp if the x-ray beam is not perfectly parallel to the edge cut direction. For this reason, the phantom plane should be made perpendicular to the central x-ray beam, and the edges utilized for the MTF measurements should be located as close as possible to the central beam. This is why region E0 (an angular square) is placed right in the middle of the phantom and is tilted at a small angle as shown in FIG. 1.

Although, all four edges of the angular square E0 can be used for MTF measurements, the two edges near regions E2 are the best. This is because region E1 is constructed from added filtration material to the phantom plate, the additional scattered x-rays from the extra material may have some negative impact to the signal near the edge transitions. Therefore, in a preferred embodiment of the present invention, only the two edges near region E2 are used for MTF measurement and are made very straight and sharp, which helps to reduce the cost in manufacturing the phantom. The edge is selected to be ~38 mm long and its tilt angle is chosen around 0.9°–7.2° (3.6° typically). Also, the distance between E0 and E1/E2 is about 45 mm. Using these design parameters allows enough room on the phantom for the E1 and E2 regions even if the smallest set of rectangular landmarks are made for the 18×24 cm storage phosphor screen.

The phantom image is acquired using a predefined incident x-ray beam quality, such as 10 mR exposure level at 80 kVp with 0.5 mm copper plus 1.0 mm aluminum filtration. The purpose of using filtration is (1) to simulate the x-ray beam spectrum encountered in practice for the general diagnostic imaging, and (2) to pre-harden the beam energy in order to minimize the impact from the target material which changes the x-ray spectrum and to improve the accuracy in measuring the system characteristics.

Phantom Image Analysis

Identifying the landmark locations in the acquired digital phantom image is important. The landmarks provide (1) geometry characteristic information regarding the imaging system, and (2) the reference points to find the locations for regions E0, E1 and E2. The detailed procedure to find the landmarks is described as follows.

Figure 4:
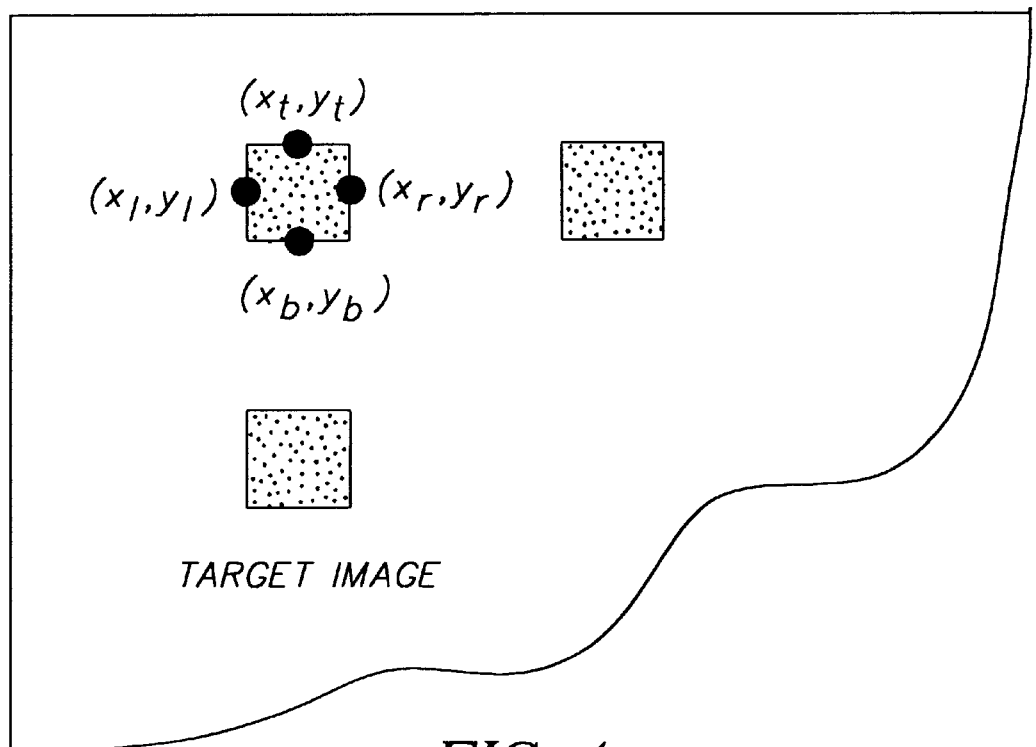

The analysis starts with a search process to identify a first landmark in the digital image, then the rest can be identified around the neighborhood of the expected location relative to the first landmark in the physical phantom and in the phantom image. Generally speaking, any one of the four landmarks at the corners of the rectangular landmark sets can be used as the first landmark. For example, for the upper-left corner, the first landmark is searched using a region growing process, as shown in FIG. 3. At the beginning of the search, a seed point $(x_0, y_0)$ is selected, which is close to the image origin (point O). To determine if the first landmark is inside the rectangular region as defined by point $(x_0, y_0)$ and point O, two profiles are calculated from the pixel line averages in the x and y directions of the rectangular region. If the landmark is completely outside, then neither profile should contain significant transitions (FIG. 3) because the landmark region corresponds to direct exposure and its periphery corresponds to exposure attenuated by the phantom plate. In this case, both the x and y coordinates of the seed point get an increment of $\Delta$, i.e., the region grows by $\Delta$ unit in both directions to point $(x_1, y_1)$. The rectangular region keeps growing until it reaches a point $(x_4, y_4)$ for example such that there is one rising transition and one falling transition that appears in at least one profile (FIG. 3), and such that the width between the two transitions is close to the physical width of the landmark. In this situation, one side of the landmark is considered to be completely within the rectangular region, and the region will stop growing in the direction where the landmark is found. However, it will keep growing in the other direction until the first landmark is also found (FIG. 3 for point $(x_5, y_5)$ as an example). Then the four boundaries of this landmark are calculated from the four significant transition points in the two profiles. The coordinates of the centers of the landmark boundaries, $(x_t, y_t)$, $(x_l, y_l)$, $(x_r, y_r)$, and $(X_b, Y_b)$, are therefore obtained, from the average of which, the center of the landmark, point $(x_c, y_c)$, is calculated too. FIG. 4 illustrates the definitions of these points.

Once the first landmark at the upper-left corner is found, the landmark next to it in the horizontal direction is searched within a window around the neighborhood of the expected location in the phantom image. To make the search more robust, the window is chosen to be a rectangular region four times as large in area as the expected landmark. Two profiles from the line averages in both x and y directions of the window are calculated and the associated properties of the landmark (FIG. 4) are calculated based on the four locations of the significant transitions in the two profiles. The newly identified landmark is used to locate the next landmark in the horizontal direction. This aggression process is repeated for the rest columns/rows of landmarks until their locations are all identified. To achieve sub-pixel accuracy in identifying the transition points, a method based on moments calculation is used due to its computational efficiency, reliability and accuracy (Ali J. Tabatabai and O. Robert Mitchell, "Edge Location to Subpixel Values in Digital Imagery," IEEE Transaction on Pattern Analysis And Machine Intelligence, Vol. 6, 1984).

Geometric properties are derived from the obtained landmark coordinates. The landmarks to be used are distributed along the perimeter of the near-maximum rectangle in the acquired phantom image. For each row/column of the landmarks along the four sides of the rectangle, ideally they should be located on a straight line, i.e., the function $$y_{ci} = k\, x_{ci} + a$$

can describe their locations completely, where $(x_{ci}, y_{ci})$, $i=0, 1, \ldots$, are the center coordinates of the landmarks, and k and a are the two fitting parameters. In a preferred embodiment of the present invention, a linear least-square-error (LSE) fit is used to find the values of k and a (William H. Press, Saul A. Teukolsky, William T. Vetterling, and Brian P. Flannery, "Numerical Recipes in C. The Art of Scientific Computing", 2nd Edition, Cambridge University Press, 1996). For example, let the slopes of the fits be $k_t$ and $k_b$ for the top and bottom rows of landmarks, respectively, the deviations of the landmark orientations from 0° are:

$$\Delta\theta_t = a\,\tan(k_t)$$

and $$\Delta\theta_b = a\,\tan(k_b),$$

respectively. Similarly, if the slopes of the fits are $k_l$ and $k_r$ for the left and right columns of landmarks, respectively, the deviations of the landmark orientations from 90° are:

$$\Delta\theta_l = -a\,\tan(k_l)$$

and $$\Delta\theta_r = -a\,\tan(k_r),$$

respectively. The overall phantom tilt, $\Delta\theta$, is defined as the average of these landmark orientations:

$$\Delta\theta = (\Delta\theta_t + \Delta\theta_l + \Delta\theta_r + \Delta\theta_b)/4.$$

The overall phantom tilt is mainly caused by (1) the phantom tilt relative to the image receptor when the image is taken, and (2) the phosphor screen tilt relative to the laser scan direction. The deviation of $\Delta\theta_t$, $\Delta\theta_l$, $\Delta\theta_r$ and $\Delta\theta_b$ from $\Delta\theta$ can indicate the transport and scan anomaly of the CR readout mechanism.

Second, comparison of the distances between the landmark center locations (or edge center points) with their actual expected distances provides information such as local pixel size and local pixel aspect ratio. Local pixel size is calculated from the ratio of the actual distance between two neighbor landmarks and the number of pixels found in between. Local pixel aspect ratio is calculated from the ratio of the local pixel size in y direction and the local pixel size in x direction. For each column/row of landmarks in the phantom image, a linear LSE fit of the distances (between every landmark and the first one) with their actual expected values, also provides important information. For example, if $(x_{ci}, y_{ci})$ and $(x_{c0}, y_{c0})$ are the center coordinates of landmark i and the first landmark, respectively, their distance in the image is $$d_i = \mathrm{sqrt}[(y_{ci}-y_{c0})^2 + (x_{ci}-x_{c0})^2].$$

If the expected distance in the physical phantom is $d_{ie}$, then a LSE fit using function $$d_i = b\, d_{ie} + \delta$$

provides values of b, $\delta$ and the $\chi^2$ of the fit, from which many parameters regarding the system characteristics are calculated, such as (1) averaged pixel size, (2) averaged pixel aspect ratio, (3) scan linearity, (4) scan accuracy, and (5) transport skew. Averaged pixel size is determined as $1/b$.

Averaged pixel aspect ratio is calculated from the ratio of the averaged pixel size in y direction and the averaged pixel size in x direction. Scan linearity and accuracy describe how linearly and accurately the phosphor screen is sampled during the readout process. They can be quantitatively characterized by $\chi^2$ of the fit, and expressed in detail by the deviation of each data point used for the linear LSE fit from the expected value obtained from the fit.

Exposure linearity and accuracy are measured from the mean values of the pixels sampled in region E0, E1, and E2. The locations of these regions are identified in the phantom image based on (a) their actual positions relative to the landmarks in the physical phantom, (b) the locations of the landmarks in the image, and (c) the overall phantom tilt angle. To minimize the impact of CR collector profile correction, only one of the two E1 regions and one of the two E2 regions are selected such that the centers of the selected regions and of the E0 region are on the same column/row of pixel lines along the slow scan direction. By defining the incident x-ray quality, such as kVp, mAs and filtration, the intensities and energy spectrum of the x-rays can be measured exactly after they penetrate region E0, E1 and E2. Therefore the expected responses (mean pixel values) and noise levels (pixel value standard deviation) for these regions of the imaging system are known. The pixel mean value of each region is defined as $$\overline{E}_i = \frac{1}{N} \sum_{k=1}^{N} p_k,$$

where N is the total number of pixels in the region, and $p_i$ is the value of pixel i. The regional standard deviation of the pixels values is $$\sigma_i^2 = \frac{1}{N-1} \sum_{k=1}^{N} (p_k - \overline{E}_i)^2.$$

When using a linear LSB fit of these expected mean values and the actual measurements (means and standard deviations), the exposure response linearity and accuracy can be characterized by the slope, offset, and $\chi^2$ of the fit. The standard deviation in each region also provides useful information regarding the system noise at that particular exposure level. Because the regions in the phantom chosen for measuring the mean and standard deviations are very small (~1×1 inch$^2$) an spot/streak artifact s in the region c an cause reduction of accuracy in measuring the standard deviation.

To address this issue, a preferred embodiment of the present invention obtains the mean and standard deviation from the median calculations. Using a rectangular region as an example, this is accomplished as follows. First, partition the rectangular region into a set of equal sized small regions, for each row, calculate their mean and variance, which are $$\overline{e}_r = \frac{1}{m} \sum_{k=1}^{m} p_k,$$

$$\eta_r^2 = \frac{1}{m-1} \sum_{k=1}^{m} (p_k - \overline{e}_r)^2,$$

respectively, where m is the number of pixels in that partition. If there are a total of n partitions, there will be n means and n variances. The median of the means and the median of the variances are therefore readily available. The median of the means is used as the overall mean of the whole region, and the standard deviation of the whole region is taken as the square root of the overall variance, which is calculated from the median of the variances. This is because the pixel values are approximately normally distributed, the variances must approximately follow a x distribution with (m−1) degree of freedom. There is a well-established relationship between the median and the mean of the $\chi^2$ distribution (Douglas C. Montgomery, "*Design and Analysis of experiments*," John Wiley & Sons, 2nd Edition). The mean of the $\chi^2$ distribution is taken as the overall regional variance. The standard deviation of all the pixels in each region are therefore obtained, which are quite robust to noise and other artifacts in the image.

Figure 5A:
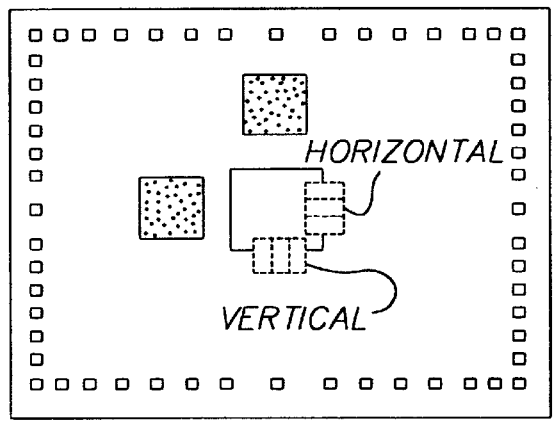
Figure 5B:
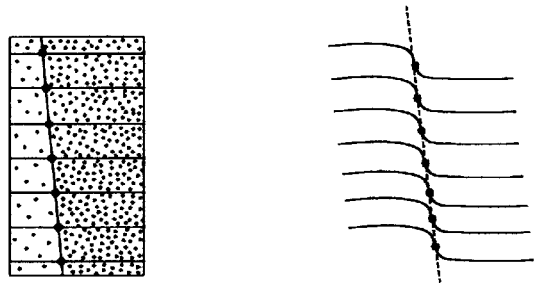
Figure 5C:
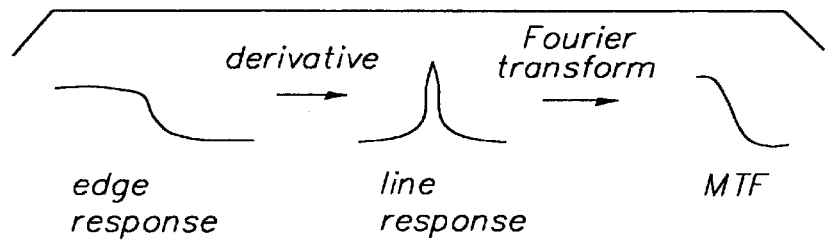

MTF measurements use two of the edges of region E0 close to region E2 as the reference objects. As shown in FIG. 5, one small region in the neighbor of either edge is extracted from the acquired phantom image for further analysis. The locations of the two regions are identified using the landmark locations as references. As shown in FIG. 5, for each step edge profile (a row of pixels) in the extracted small region, the edge transition point is estimated using the Tabatabai's method. With all the estimated points of the step edge transition points, a linear LSE fit of the (x, y) coordinates is then conducted to find the best fit of the physical sharp edge location in the image. The intersection of the fitted line with each step edge profile is defined as the actual transition point. The distance from individual edge transition point to the actual transition point describes the pixel placement error in a CR system. These step edge profiles are then aligned along their actual transition point and averaged to generate the system step edge response function (Stephen E. Reichenbach, Stephen K. Park, and Ramkumar Narayanswamy, "Characterizing Digital Image Acquisition Devices," Optical Engineering, Vol. 30, No. 2, 1991). To avoid aliasing effects, the pixel size for re-sampling of the averaged step edge response function is at least one half of the pixel size of the originally acquired phantom image. In a preferred embodiment of this work, the selected pixel size is actually one quarter of the original size.

FIG. 5 shows the major steps to obtain the MTF function from the edge response function: (1) take the derivative of the edge response to obtain line response function, (2) calculate the Fourier transform of the line response function to obtain the MTF. This process is performed for both edge transitions in FIG. 5 to obtain the MTF measurements in both x and y directions. It should be mentioned here that the actual measured averaged pixel size is used for the calculation.

A large area in the phantom image is quite useful for noise power spectrum analysis, the method of which is described in the next section.

Flat-Field Image Analysis

The flat-field image is acquired using a predefined x-ray exposure technique. This technique can be the same as the one used for the phantom image in order to simplify the QA procedure. Some parameters obtained, such as noise etc., are therefore specific to the corresponding x-ray technique only.

The system noise is characterized by its NPS (noise power spectrum), which is analyzed from the flat field image. To eliminate the effects of low frequency non-uniformity in the flat field image, such as exposure fall off, subtle screen mottle and the boundary effect, and any banding that may be introduced by the transport system, a set of 10×10 non-overlapping blocks of 128×128 pixel regions are selected around the image center for averaging. For each small image block, a 2D Fourier analysis is preformed. The power spectra of all the blocks are summed together to provide an averaged result. This analysis provides a 2D noise spectral surface. Later, "cuts" of this surface are determined by averaging data in the vicinity of the two axes in the frequency space with values on or adjacent to the axes being ignored. Such obtained two 1D plots are functions of spatial frequency and are considered as the NPS of the imaging system in x and y directions. For a nominal system, its NPS in neither direction should be higher than a predefined threshold, which is also a 1D function of spatial frequency. It should be mentioned that, peaks in the NPS correspond to coherent noise present in the system.

Figure 7:
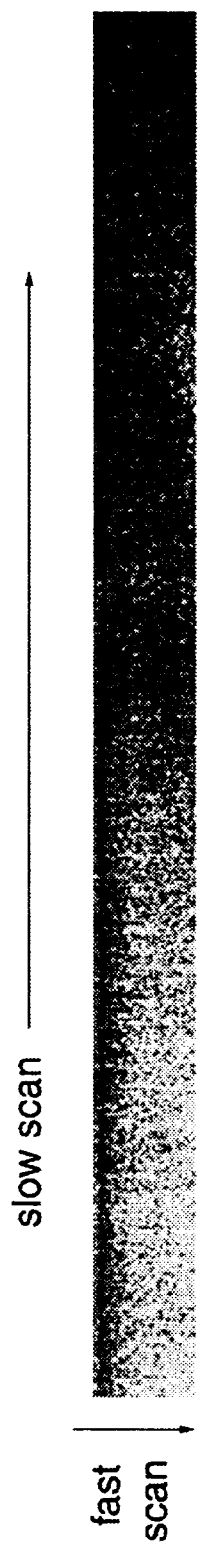

Beside NPS, many other characteristics of the imaging system can be measured form the flat field image, such as galvo wobble, transport banding artifact, streak artifact, and field uniformity etc. Galvo wobble is specific only to CR and is most obvious at the beginning of each fast scan (see FIG. 7) in one type of CR reader a laser beam is scanned across the storage phosphor screen by a reciprocating mirror driven by a galvo. To detect and quantify the galvo-jitter artifact, a small band along the slow scan direction is extracted at the beginning of the fast scan. This band is averaged along the fast scan direction and 1D Fourier power spectrum is calculated in the band direction. The total power energy beyond certain high frequency is summed as the magnitude of the galvo-wobble artifact.

For field uniformity check, the image is equally partitioned into a set of small and non-overlapping regions. The mean of each small region is calculated and its deviation from the overall mean of the whole image is reported. Usually a 4×4, 5×5, or 8×8 partition is recommended.

A dominant artifact for CR images is the banding artifact caused by transport of the storage phosphor in the slow can direction. It is periodic in the slow scan direction and its frequency is specific to the particular design of the CR imaging system. Therefore, Fourier power spectrum is suitable to detect and characterize this artifact. First, a number of pixel lines along the slow scan direction are sampled from the flat field image. These lines are averaged for random noise reduction. Second, Fourier transform is conducted and the energy of the spectrum is calculated. Third, around the neighbor of the particular frequency point where the transport banding artifact is expected, the local maximum is identified and the excess area under the peak is calculated as the magnitude of the transport banding artifact.

Because streak artifacts are usually in either the x or y directions of the image, the detection of such artifacts is based on the detection of isolated peaks in the two 1D profiles of the column/row averages of the image pixels. The isolated peaks can be identified using the 1D morphological closing/opening filtering technique (R. C. Gonzalez and R. E. Woods, "*Digital Image Processing*," Addison-Wesley Publishing Company, 1993). The width of the filter is recommended being larger than the widest streak in the image. The location and the magnitude of each peak are reported.

Erased Image Analysis The erased image represents the inherent baseline noise of the digital x-ray imaging system along the whole image acquisition path. This image may contain the "ghost" image from the previous exposure if the image receptor is not fully erased. Also, a coherence noise can be observed in the image if the readout process is interfered with by the 60 Hz frequency signal from the power supply. For CR, collector banding artifact can be quite obvious if the collector profile is not acquired properly. For DR, bad or non-consistent performing pixels, data/control/ gate lines, or preamplifier cause spot/steak artifacts. Therefore, the goal for the erased image analysis is to examine the system baseline signal level, erase function completeness, collector profile anomaly, coherence noise level, and artifacts, etc.

The analysis of the erased images starts with artifact inspection, such as spot, streak, and coherent noise. Positive/negative going spot clusters in the image are detected using a 2D morphological opening/closing filtering technique. The size of the morphological filter is recommended being wider than the largest spot size to be detected. The location and pixel population of each spot cluster are recorded and reported. The total number of spot clusters is counted and reported too. Later all the spot artifacts are removed from the erased image for further artifact analysis. Streaks are usually 1D artifacts in either x or y direction, and they can be detected from the two profiles obtained from the column/row averages of the spot removed erased image. Again, 1D morphological opening/closing filtering is used for this purpose. The location and magnitude of the streak artifacts are reported.

Figure 6:
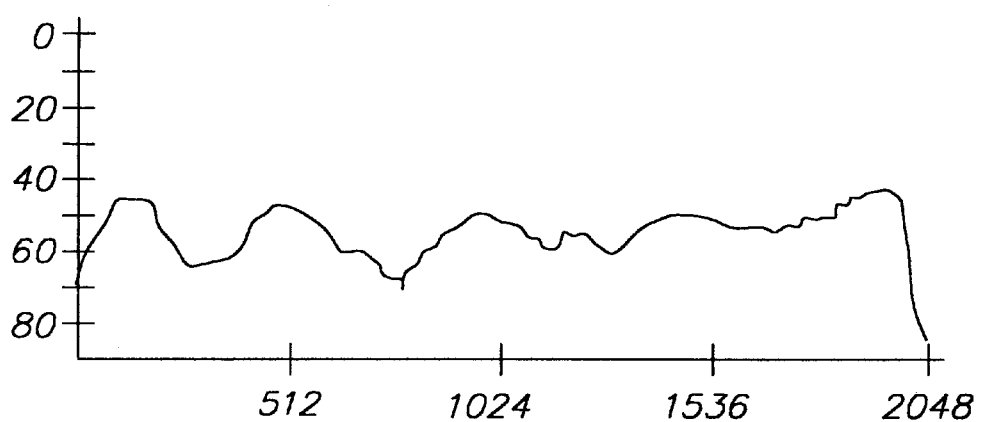

For CR, the pixel average along the slow direction scan contains the collector profile(FIG. 6). The mean and maximum of this profile are calculated. If the calculated mean is beyond a certain threshold, it could be caused by (1) the erase function of the system is not working properly, which causes some residual signal; (2) the electronics of the system has certain drift; or (3) the collector profile is not correct. A 2D Fourier transform of the erased image is used for coherent noise detection. Because the frequency of the coherent noise is often specific to imaging system, the detection process is to look for isolated peaks in the Fourier energy spectrum around the predetermined frequency range (s). Again the 2D morphological opening/closing filtering technique is recommended for this purpose.

PARTS LIST

10 CR imaging system
12 x-ray source
14 object
16 storage phosphor
18 CR reader
20 image processor
30 DR imaging system
32 DR detector
40 x-ray digital radiography imaging system
42 phantom
44 image detector
46 image processor

What is claimed is:

1. A phantom for use in measuring characteristics of a digital radiography image system comprising:

a substantially flat member of an x-ray attenuating material;

a first array of landmarks associated with said member to be imaged within but close to the boundary of the image receptor and to be used for use in geometry measurements including pixel size, pixel aspect ratio and scan linearity;

a set of regions associated with the central position of said member for exposure linearity accuracy and noise measurement; and a set of sharp angular edges associated with the central position of said member for modulation transfer function measurements.

2. The phantom of claim 1 wherein said member is formed from one or more of metals including copper, aluminum, lead.

3. The phantom of claim 1 wherein said first array of landmarks include one of apertures in said member of x-ray attenuating material attached to said member.

4. The phantom of claim 1 wherein said first array of landmarks including one of square, circular, or rectangular shape.

5. The phantom of claim 1 wherein said set of regions include at least first and second regions of different x-ray attenuation.

6. The phantom of claim 1 wherein said set of regions includes a structure defining a hole in the center of said phantom; and wherein said set of sharp angular edges form part of said hole.

7. The phantom of claim 1 wherein said first array of landmarks are designed for different image receptors.

8. The phantom of claim 1 wherein said phantom is used with a frame of the same size, which has a hole in its middle to hold a smaller image receptor in order to center and align with said phantom.

9. The phantom of claim 1 has an x-ray dose meter attached in order to measure the entrance x-ray exposure level.

10. The phantom of claim 3 wherein said aperture is made by photoetching process.

11. In a digital radiographic imaging system including a variable source of x-rays, and x-ray image receptor, a digital image processor, a method of measuring pre-selected parameters of said system comprising:

erasing the image photoreceptor and exposing said image receptor to a flat field x-ray image at a predetermined x-ray exposure level from said x-ray source to produce a digital flat field x-ray image;

erasing the image receptor immediately after a relatively high x-ray exposure level from said x-ray source to produce a digital dark erased x-ray image;

exposing said image receptor to x-rays from said x-ray source projected through a phantom haying regions of different x-ray attenuation to produce a digital phantom x-ray image; and processing in said digital image processor said digital x-ray images to determine parameters of said digital radiographic imaging system.

12. The method of claim 7 wherein said digital phantom x-ray image is processed in said digital image processor for one or more of spatial resolution, exposure response, geometric distortions, noise, and geometric distortions of said system.

13. The method of claim 8 wherein said digital dark erased x-ray image is processed in said digital image processor for dark image noise analysis of said system.

14. The method of claim 7 wherein said digital flat field x-ray image is processed in said digital image processor for system artifact, noise and response uniformity of said system.

15. The method of claim 12 wherein said exposure response (pixel value mean) and said noise (pixel value standard deviation) is calculated by the following steps:

a. partition the region to be analyzed into a set of small and equal partitions; and b. calculate the mean and variance of each partition; and c. use median of the mean as said exposure response;

d. calculate median of variances followed by calculating mean of variances based on $\chi^2$ distribution; and e. calculate noise as square root of mean of variances.

* * * * *